United States Patent [19]

Chan

[11] Patent Number: 5,242,421

[45] Date of Patent: Sep. 7, 1993

[54] NEEDLE CAP

[76] Inventor: Mark S. H. Chan, 919, Lotus House, So Uk Estate, Kowloon, Hong Kong

[21] Appl. No.: 925,387

[22] Filed: Aug. 4, 1992

[30] Foreign Application Priority Data

Aug. 6, 1991 [AU] Australia ............................ PK7630

[51] Int. Cl.$^5$ .............................................. A61M 5/32
[52] U.S. Cl. .................................... 604/198; 604/192
[58] Field of Search ............... 604/192, 197, 198, 263; 206/364, 365, 367

[56] References Cited

U.S. PATENT DOCUMENTS

| 4,950,242 | 8/1990 | Alvarez ........................... 604/192 X |
| 5,017,189 | 5/1991 | Boumendil ......................... 604/192 |
| 5,037,401 | 8/1991 | DeCamp ........................... 604/192 |
| 5,046,612 | 9/1991 | Mostarda et al. ............... 604/192 X |

FOREIGN PATENT DOCUMENTS 9107199  5/1991  World Int. Prop. O. .......... 604/192

Primary Examiner—Robert P. Swiatek
Attorney, Agent, or Firm—Gunn, Lee & Miller

[57] ABSTRACT

A needle cap having a generally elongate configuration with an elongate channel extending axially therein to receive and hold a needle of a syringe by transverse movement of the needle relative to the longitudinal axis of the cap. A channel is closed at one end to protect the point of the needle when engaged with a cap and the opposite end is open. The needle has an integral base for engaging the needle to the syringe and the integral base mates with a recess in the channel such that the needle is releasably retained in a first position and fixedly retained in a second position.

7 Claims, 2 Drawing Sheets

NEEDLE CAP

BACKGROUND OF THE INVENTION

The present invention relates to a needle cap and in particular to a needle cap for removably and safely capping a needle with a syringe.

Many types of needle caps are known which are employed to render safe needles before and after use. Needles are also disposed of with the caps in place. A needle cap is employed to prevent a syringe user from being stabbed or injured by the needle of the syringe.

Needle caps are required for at least some of the following specific reasons.

1. To protect users during disassembly of a syringe from exposed contaminated needles.
2. To protect users from exposed needles when several have to be carried to a disposal box.
3. To safely store a needle between uses i.e. where its contents are to be administered in two or more doses at different times.
4. To protect others including handlers of waste needles, person(s) in the presence of a needle user etc.

In this regard, it is important to ensure that a needle cap is easily and safely fitted and removed, and optionally can be adjusted whilst fitted so that it is no longer easily removed. Furthermore, it is important that the needle cap can be fitted so that there is no risk of the user stabbing or injecting themselves with the needle of the syringe. In this regard, the needle cap should allow a motion of fitting and removal to and from a needle so that the needle is generally directly away from the user, and in particular away from the thumb and finger holding the cap.

SUMMARY OF THE INVENTION

Accordingly, the present invention provides a needle cap of generally elongate configuration having an elongate channel therein adapted to receive and hold a needle of a syringe by transverse movement of the needle relative to the elongate axis of the cap, the channel having one closed end protecting the point of the needle when engaged with the cap, and an opposite open end.

Preferably the needle has an integral base adapted to be engaged with the syringe.

It is preferred that the channel is arranged to releasably retain the needle and the base in a first position within the channel, and fixedly retain the needle and base in a second position within the channel.

By the term "fixedly retain(ed)" as used throughout the specification, it is meant that the needle and base become fixed in the channel such that only excessive user force can remove the needle and support from the channel. In disposal of the needle and base for example, it is preferred that the needle and base be "fixedly retained" in the channel.

Preferably the needle cap is substantially rectangular in external cross section.

Preferably the needle cap further comprises shielding means integral with the channel and arranged to receive and cover the tip of the needle when the needle and base are in the second position.

Preferably the shielding means includes a cover extending over the closed end of the channel for receiving and covering the tip of the needle.

Preferably the base of the needle is releasably retained or fixedly retained in the channel by locking means provided within the channel.

Preferably the locking means includes a cavity provided in the channel adjacent the open end, the cavity being shaped to receive the needle base.

Preferably the locking means further includes at least one protuberance extending inwardly from side walls of the channel in and adjacent the cavity wherein the or each protuberance is arranged to releasably retain the needle base in the cavity in said first position and fixedly retain the needle base in the cavity in said second position.

Preferably each side wall of the channel has an inwardly and downwardly sloping face extending from its upper edge, which faces define an elongate gutter between their respective lower edges. Preferably the gutter extends part way through the channel from a point under the cover to the cavity, the gutter being parallel to the side walls an arranged to receive the needle.

The present invention also provides a needle base for use with the needle cap of the present invention, the base having one or more radial protuberances arranged to be engageable with the locking means in the needle cap.

BRIEF DESCRIPTION OF THE DRAWINGS

A preferred embodiment of the invention will now be described, by way of example only, with reference to the accompanying drawings in which.

DETAILED DESCRIPTION OF THE PREFERRED EMBODIMENT

Figure 1:
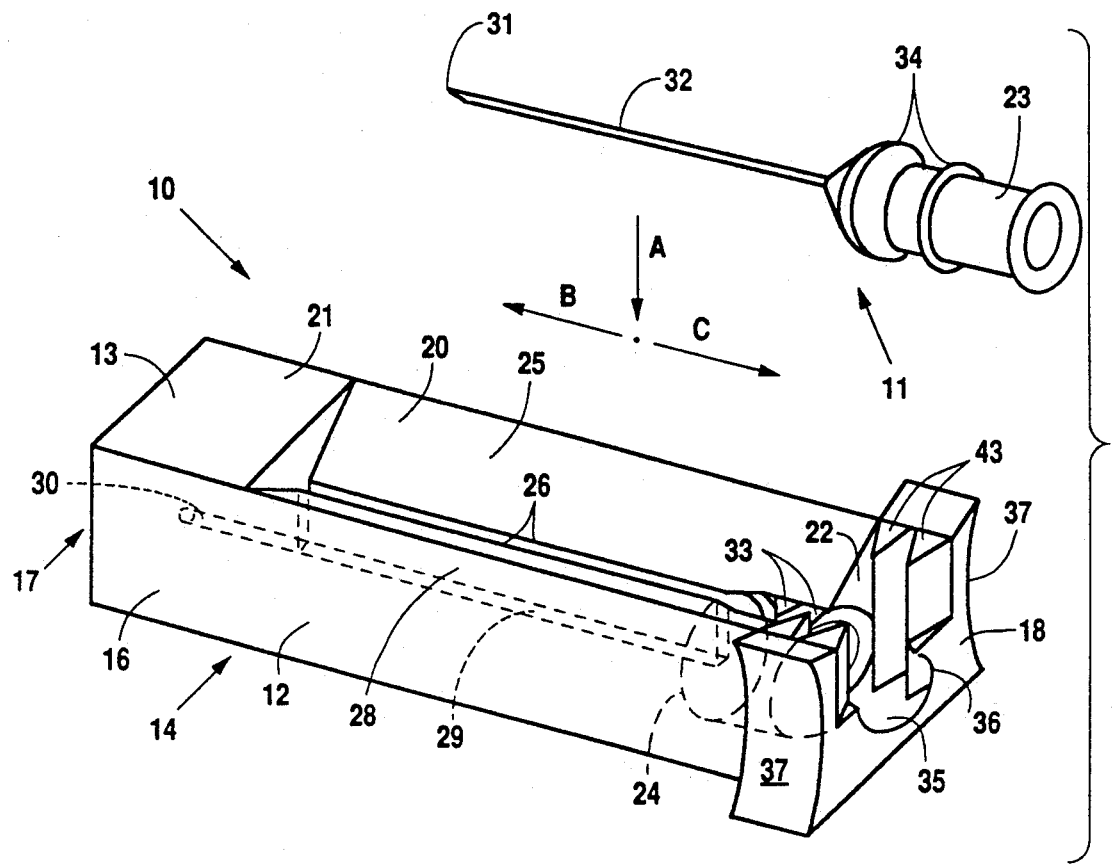
FIG. 1 is a perspective view of a needle cap according to the invention with a needle and base to be fitted therein.
Figure 5:
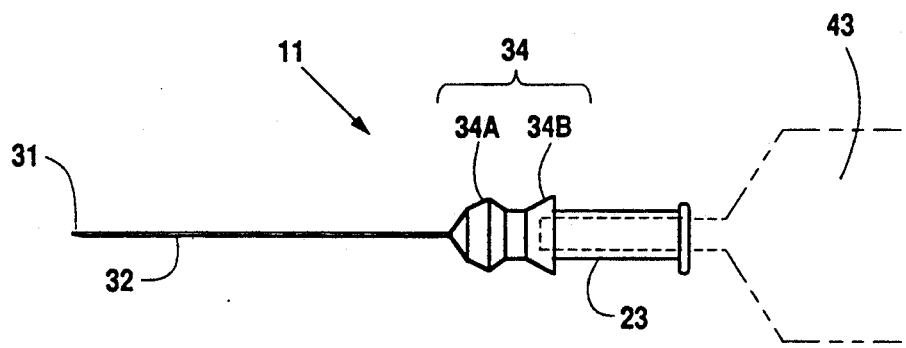
FIG. 5 is a side view of a needle and base according to the present invention.

Referring to the drawings, a needle cap 10 for removably capping a needle and base is elongate and generally of channel shaped section 12. Integral with the cap are shielding means in the form of a closed end compartment 13.

The rectangular section channel is defined by a base 14, side walls 16, end walls 17 and 18 and has an open top 20.

The compartment 13 is defined by a portion of the side walls 16, end wall 17 and a cover 21.

A rectangular channel 22 open at the top 20 is provided in open end wall 18 for receiving a portion of needle base 23. Channel 22 provides an opening to cavity 24, which is also upwardly open at open top 20.

The side walls 16 are provided with sloping inner walls 25 which extend between compartment 13 and cavity 24. The walls 25 slope inwardly and downwardly and terminate at their bases 26 to define a gutter 28 which extends downwardly to passage 29 and between the cavity and compartment 13. A needle recess 30 extends from passage 29 into compartment 13, for receiving and shrouding the tip 31 of the needle 32.

Protuberances in the form of ridges 43 are provided in the rectangular channel 22 and extend inwardly into the channel from the side walls 16. These ridges are arranged to engage corresponding radial ridges 34 that protrude from the needle base 23. Similar annular ridges 33 are provided in cavity 24.

A recess 35 is provided in the open end wall 18 at the end of the rectangular channel 22. The recess 35 is upwardly open and has curved inner walls 36 which receive and hold in place the needle base 23, to prevent lateral movement thereof.

The cap is also provided with wings 37 which can be held by a user to avoid needle contact.

Figure 2:
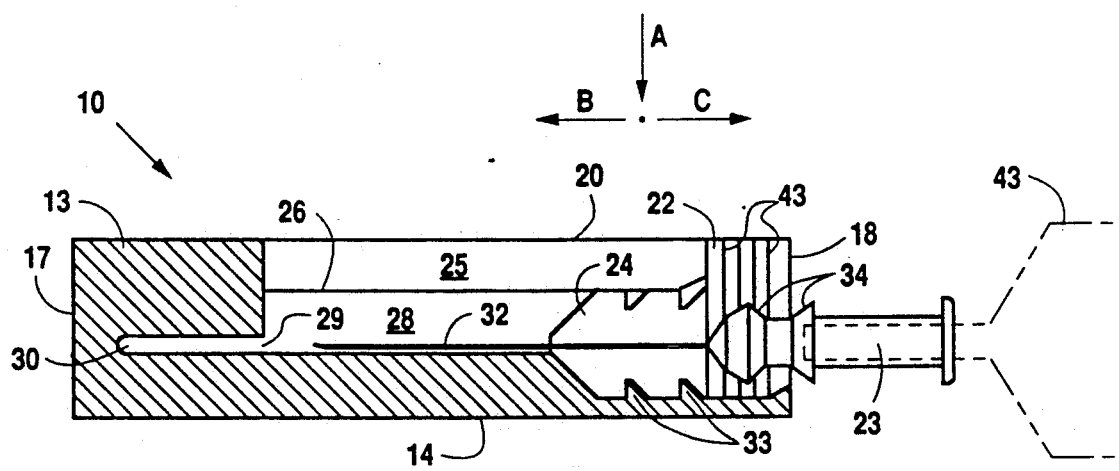
FIGS. 2 to 4 are longitudinal cross-sectional elevational views of the needle cap shown in FIG. 1 with the needle and base fitted at various positions therein.

In use, needle and base 11 are guided into the rectangular channel 22 by transverse movement of the needle relative to the elongate axis of the cap in the direction of arrow A (FIGS. 1 and 2) so that the needle 32 is directed via sloping walls 25 into gutter 28 and passage 29 and the needle base 25 is simultaneously directed into cavity 24 engaging curved inner walls 36 as shown in FIG. 2.

Figure 3:
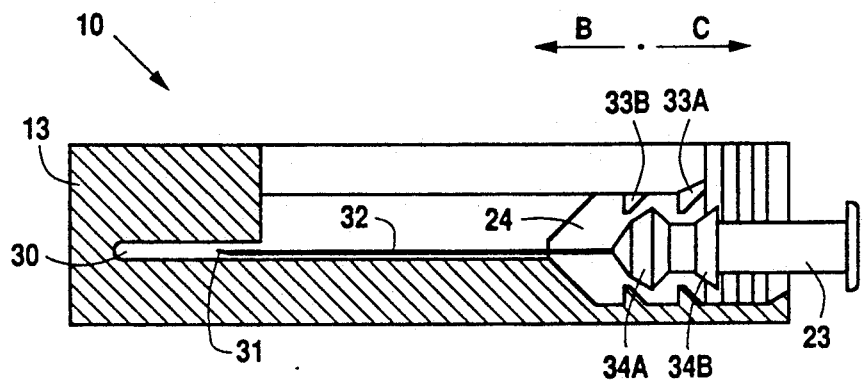

The needle and base 11 are then forced in direction B along the longitudinal axis from the initial position shown in FIG. 2 to a releasable position as shown in FIG. 3. In so doing, a first radial ridge 34A on the needle base passes a first cavity ridge 33A to releasably retain the needle and base. In this position the needle tip is located within the needle recess 30 to protect the needle. If the needle and base 11 is to be used further it can be withdrawn from this position by applying a force to the syringe 40 (shown in phantom in FIG. 2 for reference only) in direction C opposite to direction B along the same longitudinal axis (FIGS. 2 and 3).

Figure 4:
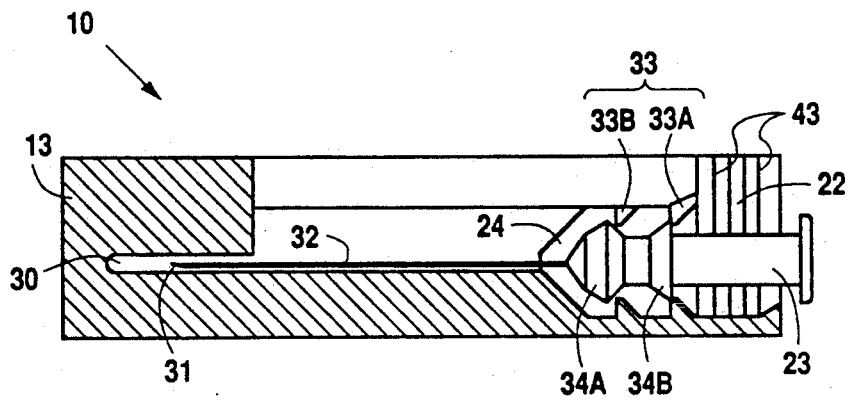

The needle and base can be fixedly retained in the cap by forcing them further in direction B to the position shown in FIG. 4 wherein the needle tip travels further into needle recess 30 and is safely and securely enclosed in compartment 13. In so moving, first radial ridge 34A will engage and pass a second cavity ridge 33B (optional) while a second radial ridge 34B will engage and pass the first cavity ridge 33A so that the needle and support become locked in place in the cap and cannot be easily removed.

Referring to FIGS. 2 to 5, it will be seen that the first radial ridge 34A slopes in both directions to enable movement in both directions (B and C) past the cavity ridges 33 whereas the second radial ridge 34B, and the cavity ridges 33 slope in one direction only and cooperate to allow relatively easy insertion of the needle base 23 (direction B) while restricting withdrawal of the needle base (direction C). Thus the cap provides both releasably retained and fixedly retained positions.

The cap, by virtue of its construction, make it possible for a user to hold the device in a way that user-needle contact is greatly minimised or avoided. That is, a user can hold the device at wing 37 and therefore distance the hand from the tip of the needle when loading the cap. Furthermore, because the needle is engaged with the cap by transverse movement of the needle, the tip of the needle is never moved toward the fingers of a user holding the cap. There is, therefore, a greatly reduced risk of the tip of the needle puncturing the skin of the fingers of the user if the needle is not correctly aligned with the cap during engagement.

Typically the needle cap and the needle base would be made from a plastics material.

The protuberances could be replaced with a suitable equivalent so that the cap could be used with conventional needle bases, i.e., bases without radial ridges. For example, a polymeric rubber annulus that engaged the external surface of the needle base inducing a friction fit between cap and base could equally well be employed.

Alternatively, a needle base with a single ridge of 34B shaped could be used with first cavity ridge 33A being of the releasable ridge construction of radial ridge 34A. Similarly, for the needle base as shown in the figures, only one cavity ridge is required although two or more ridges may be desired.

The cap can also be releasably mounted on any flat surface to avoid the need to handle the cap during loading and removal of a needle. This would virtually eliminate any chance of user-needle contact.

Typical examples of releasable mounting techniques include incorporating a magnetic strip in or on the base 14 of the needle cap or applying a coating of releasable adhesive to the base 14, or a part thereof.

Whilst the invention has been described with reference to a particular example, it will be appreciated that the invention can be embodied in many other forms, and applicable in disposal of intravenous cannulas, and tubing connections involving sharp ends.

I claim:

1. A needle cap of generally elongate configuration having an elongate channel therein receiving and holding a needle of a syringe by transverse movement of said needle relative to an elongate axis of said cap;

said channel having one closed end protecting a point of said needle when engaged with said cap, and an opposite open end;

said needle having an integral base adapted to be engaged with said syringe and said channel is arranged to releasably retain said needle and said base in a first position within said channel, and fixedly retain said needle and base in a second position within said channel;

said base of said needle is releasably retained or fixedly retained in said channel by locking means provided within said channel;

said locking means includes a cavity provided in said channel adjacent said open end, said cavity having curved inner walls shaped to receive said needle base;

wherein said locking means further includes at least one protuberance extending inwardly from side walls of said channel in and adjacent said cavity wherein a or each protuberance is arranged to releasably retain said needle base in said cavity in said first position and fixedly retain said needle base in said cavity in said second position in cooperation with at least one radial protuberance formed on said needle base.

2. A needle cap as defined in claim 1 wherein each side wall of said channel has an inwardly and downwardly sloping face extending from an upper edge, which faces define an elongate gutter between respective lower edges.

3. A needle cap as defined in claim 2 wherein said locking means includes a cavity provided in said channel adjacent said open end and said gutter extends part way through said channel from said cavity to a point adjacent a shielding means, said gutter being parallel to said side walls and arranged to receive said needle.

4. A hypodermic assembly comprising a hypodermic needle for a syringe and a needle cap;

said needle having an integral base adapted to be engaged with said syringe, said base having at least one radial protuberance formed thereon;

said cap further comprising:

a generally elongate configuration with a elongate channel therein adapted to receive and hold said needle by transverse movement of said needle relative to a longitudinal axis of said cap, said channel having a closed end and an opposite open end;

locking means comprising a cavity formed in said channel adjacent said open end, with curved inner walls shaped to receive said base and having at least one protuberance extending inwardly from side walls of said channel in and adjacent said cavity and cooperating with said at least one radial protuberance formed on said base to releasably retain said needle in a first position within said channel and fixedly retain said needle in a second position within said channel; and shielding means integral with said channel to receive and cover a tip of said needle when said needle is in said second position.

5. A hypodermic assembly as defined in claim 4, wherein said shielding means includes a cover extending over said closed end of said channel for receiving and covering said tip of said needle.

6. A hypodermic assembly as defined in claim 4, wherein each side wall of said channel has an inwardly and downwardly sloping face extending from its upper edge, which faces define an elongate gutter between their respective lower edges.

7. A hypodermic assembly as defined in claim 6, wherein said gutter extends part way through said channel from said cavity to a point adjacent said shielding means, said gutter being parallel to said side walls and arranged to receive said needle.

* * * * *